United States Patent [19]

Morrison

[11] Patent Number: 4,619,274
[45] Date of Patent: Oct. 28, 1986

[54] TORSIONAL GUIDE WIRE WITH ATTENUATED DIAMETER

[75] Inventor: David W. Morrison, San Jose, Calif.

[73] Assignee: Advanced Cardiovascular Systems, Inc., Mountain View, Calif.

[21] Appl. No.: 724,624

[22] Filed: Apr. 18, 1985

[51] Int. Cl.$^4$ .............................................. A61B 5/00
[52] U.S. Cl. .................................. 128/772; 128/657; 604/170
[58] Field of Search ...................... 128/749, 772, 657; 604/95, 170, 280, 282

[56] References Cited

U.S. PATENT DOCUMENTS 4,554,929 11/1985 Samson et al. ...................... 128/772

Primary Examiner—Kyle L. Howell
Assistant Examiner—Randy Citrin
Attorney, Agent, or Firm—Flehr, Hohbach, Test, Albritton & Herbert

[57] ABSTRACT

Guide wire having a progressively attenuated diameter comprising an elongated core element having proximal and distal ends and having a decreasing cross sectional area in a direction towards the distal end. A coil is carried by and secured to said core element an has proximal and distal ends. The coil has a diameter which decreases in a direction towards the distal end. The coil is formed of a wire which has a diameter which decreases from one end to the other end and which is wound in a helix so that the larger diameter wire begins in a region closer to the proximal end and the smaller diameter wire ends in a region closer to the distal end.

9 Claims, 9 Drawing Figures

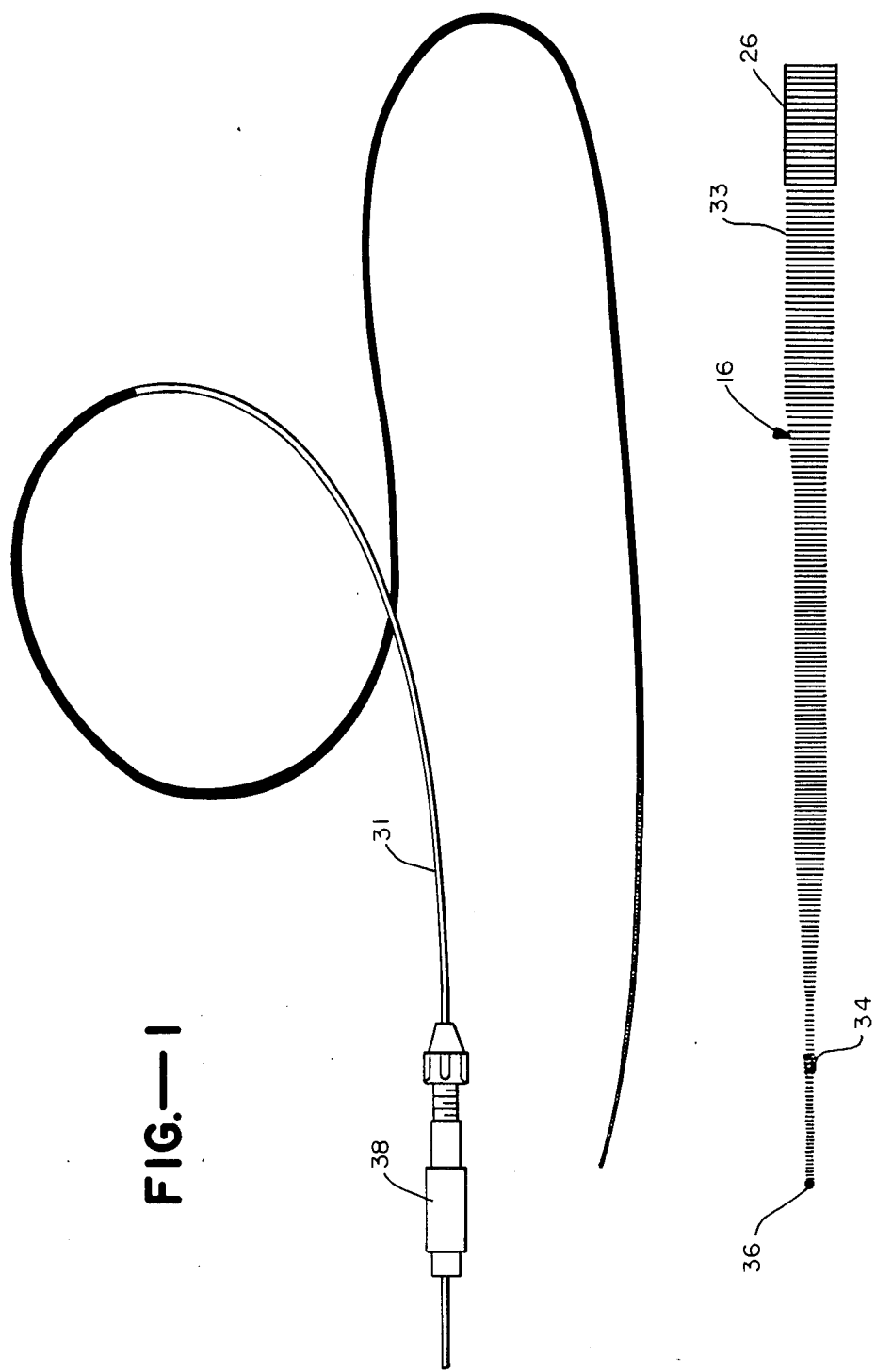

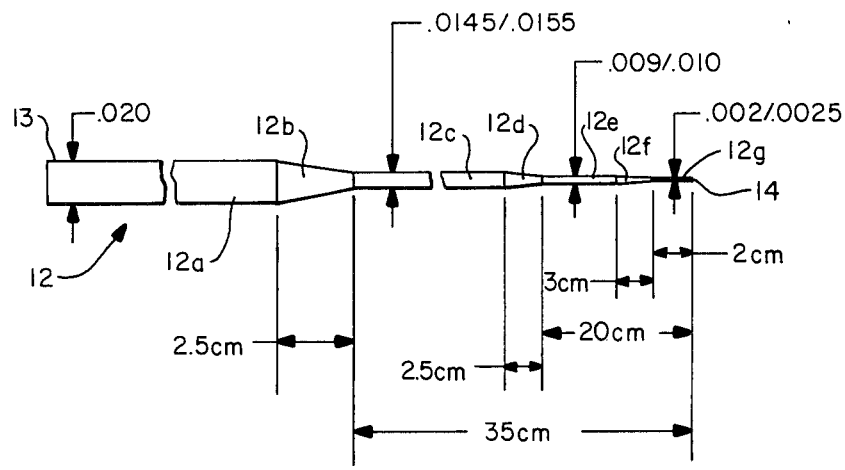
FIG. —3
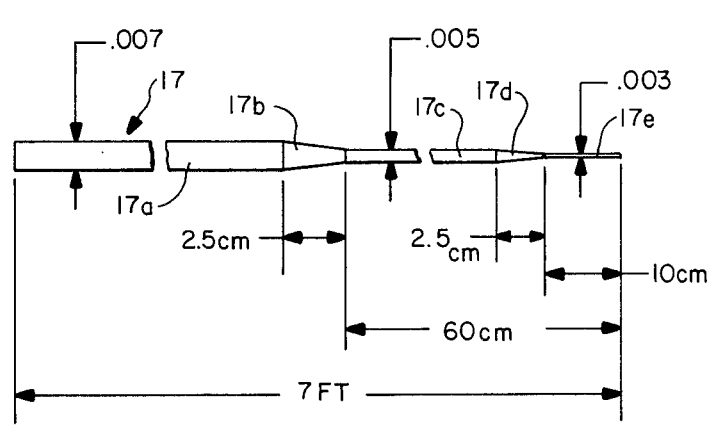
FIG. —4
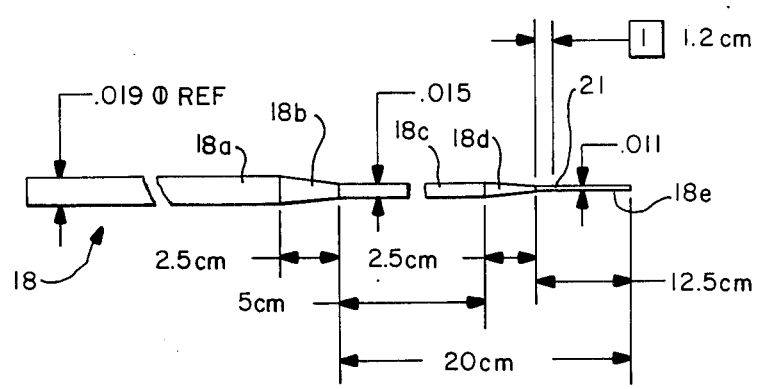
FIG. —5

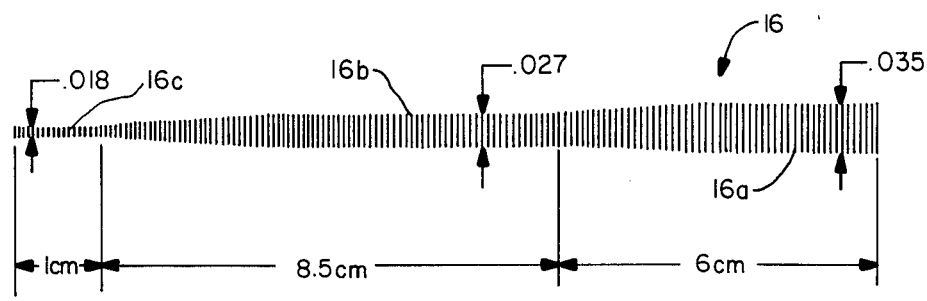
FIG. — 6
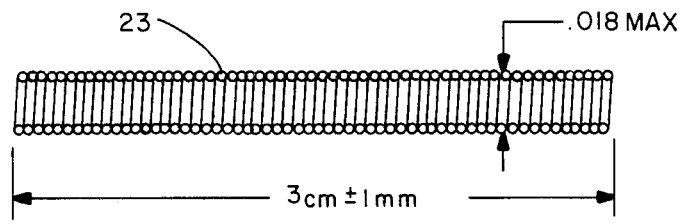
FIG. — 7
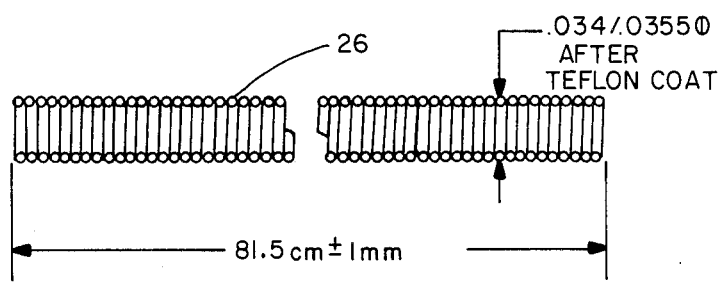
FIG. — 8
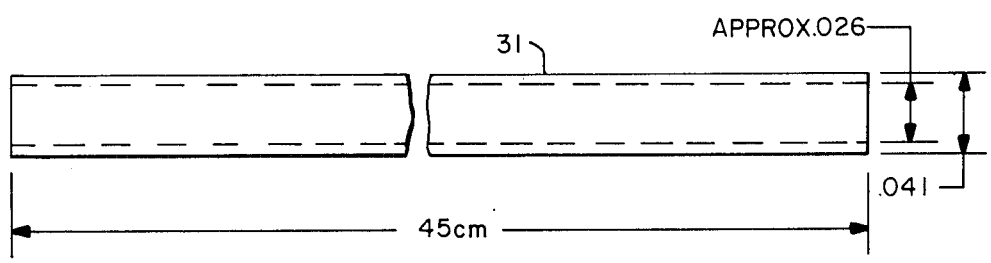
FIG. — 9

TORSIONAL GUIDE WIRE WITH ATTENUATED DIAMETER

This invention relates to guide wires for use with catheters and more particularly, to guide wires with an attenuated diameter and having torsional control.

Guide wires heretofore have been provided, however, guide wires which make it possible to penetrate small blood vessels with adequate proximal strength for catheter tracking capabilities as, for example, in the kidney and which still permit high torsional capabilities have not been available. There is therefore a need for a torsional attenuating diameter guide wire.

In general, it is an object of the present invention to provide a guide wire which has a progressively attenuated diameter.

Another object of the invention is to provide a guide wire of the above character which has high torsional capabilities.

Another object of the invention is to provide a guide wire of the above character which is provided with a small tip facilitating deep penetration into small vessels.

Another object of the invention is to provide a guide wire of the above character which has a relatively large proximal diameter to facilitate tracking of the catheter while it is in use.

Additional objects and features of the invention will appear from the following description in which the preferred embodiment is set forth in detail in conjunction with the accompanying drawings.

FIG. 1 is a side elevational view of a torsional guide wire with a progressively attenuated diameter incorporating the present invention.

FIG. 2 is an enlarged view of the distal extremity of the guide wire shown in FIG. 1.

FIG. 3 is a side elevational view of the core utilized in the guide wire shown in FIG. 1.

FIG. 4 is a side elevational view of the wire utilized for making the tapered coil for the guide wire in FIG. 1.

FIG. 5 is a side elevational view of the winding mandrel for the tapered coil of FIG. 6.

FIG. 6 is a side elevational view of the tapered coil made from winding the wire of FIG. 4 onto the mandrel of FIG. 5.

FIG. 7 is a cross sectional view of the platinum coil tip utilized in the guide wire shown in FIG. 1.

FIG. 8 is a cross sectional view of the proximal coil utilized in the guide wire shown in FIG. 1.

FIG. 9 is a side elevational view of the plastic tubing utilized in the guide wire shown in FIG. 1.

In general, the torsional guide wire with a progressively attenuated diameter is comprised of an elongate core element having proximal and distal ends and having a decreasing cross sectional area in a direction towards the distal end. It is also comprised of a coil carried by and secured to the core element and extends over the distal extremity of the core element. The coil has proximal and distal ends and has a diameter which decreases in a direction towards the distal end. The coil is formed of wire which has a diameter which decreases from one end to the other end and is wound in a helix so that the larger diameter wire begins in a region closer to the proximal end and the smaller diameter wire ends in a region closer to the distal end.

More in particular as shown in FIGS. 1 and 2 of the drawings, the attenuating diameter guide wire 11 consists of a core element 12. The core element 12 is shown in detail in FIG. 3 and is formed of a suitable material such as stainless steel and has a suitable diameter such as from 0.015 to 0.025 and preferably a diameter of 0.02, plus or minus 0.0003 and having a suitable length such as 7 feet. The core element is provided with proximal and distal ends 13 and 14. The core element 12 is centerless ground to provide a core wire which has a decreasing cross sectional area in a direction towards the distal end. Thus as shown, the core element 12 is provided with a cylindrical portion 12a which extends over a major portion of the length of the core element. A tapered portion 12b adjoins the portion 12a and extends over a suitable distance such as 2½ centimeters and provides a taper, for example, from 0.02 inches to 0.0145 to 0.0155 inches and preferably a dimension of 0.015 inches. The remaining length of the core element is centerless ground to a dimension such as 0.015 inches for a length of approximately 35 centimeters. Thereafter, in a further grinding operation a transition region 12d is provided which over a length of approximately 2.5 centimeters provides a transition from 0.015 to 0.009 to 0.01 inches. The following portion 12e of approximately 10 centimeters is centerless ground to the 0.01 inch dimension. Thereafter an additional transitional region 12f is provided which provides a transition from 0.01 inches to 0.002 to 0.0025 inches. This transition extends over approximately 3 centimeters. The remaining distal extremity of the core wire as, for example, a length of approximately 2 centimeters is ground so that it has a diameter of 0.002 to 0.0025 inches. Thus it can be seen that a core element has been provided which has been carefully dimensioned by centerless grinding to provide a decreasing cross sectional area or a taper as hereinbefore described.

The guide wire 11 also consists of a tapered coil 16. The coil 16 itself is shown in FIG. 6. The wire 17 from which it is wound is shown in FIG. 4. The mandrel 18 on which the wire 17 is wound to form the coil 16 is shown in FIG. 5. The wire 17 is formed of a suitable material such as stainless steel and has a length of approximately 7 feet and a diameter of 0.007 inches plus or minus 0.0002 inches. A major portion of the wire 17 has an outer dimension of 0.007 but the remainder of the wire is centerless ground to provide a decreasing diameter towards the distal extremity of the wire. Thus in addition to the cylindrical portion 17a there is provided a transition portion 17b of a suitable length such as 2.5 centimeters in which there is a dimension change from 0.007 inches to 0.005 inches for a length of approximately 60 centimeters from the distal extremity of the wire. A portion 17c of the wire has a diameter of 0.005 inches. At another portion, 17d of the wire, another transition in diameter is made over a distance of approximately 2.5 centimeters from 0.005 inches to 0.003 inches. There is then provided a portion 17e having a length of approximately 10 centimeters which has a diameter of 0.003 inches.

The mandrel 18 on which the wire 17 is wound is shown in FIG. 6 and is formed of a suitable material such as steel having a diameter of 0.019 inches extending over the portion 18a. A transition portion 18b is provided extending over 2½ centimeters in which the diameter is decreased from 0.019 to 0.015 inches. Another portion 18c is provided having a diameter of 0.015 inches extending up to another transition portion 18d in which the diameter is decreased to 0.011 inches so that the distal extremity of the mandrel provided by the portion 18e has a diameter of 0.011 inches and a length of approximately 12.5 centimeters.

The coil or coil section 16 is then formed by taking the wire 17 and taking the end of the smallest diameter and starting it on the mandrel at the point 21 and progressively winding the wire onto the mandrel 18 in a helix in a direction towards the larger diameter end over a distance of approximately 15.5 centimeters. Thus, the larger diameter wire begins in a region closer to the proximal end and the smaller diameter wire ends in a region closer to the distal end of the coil 16. After the winding has been completed, the core or coil section 16 can be removed from the mandrel and trimmed to length. The proximal and distal ends of the coil 16 can be stretched apart slightly so that the ends can be screwed together with other coils or coil sections as hereinafter described.

The coil section 23 which forms the tip of the guide wire 11 is formed of a suitable wire such as a platinum alloy having a diameter of 0.003 inches plus or minus 0.0002 inches. This wire 11 is 3 centimeters plus or minus one millimeter and having an outside diameter of approximately 0.018 inches maximum. The interior diameter corresponds to the diameter of the mandrel which is approximately 0.011 inches. One end of the coil 23 is stretched so as it make it possible to screw into another coil end as hereinafter described.

The coil or coil section 16 after being wound or removed from the mandrel is formed so that it is provided with a portion 16a having an outside diameter of approximately 0.035 inches, another portion 16b having an outside diameter of approximately 0.027 inches and a distal extremity 16c having an outside diameter of approximately 0.018 inches.

Another core or coil section 26 is provided which can be identified as the proximal coil. This coil is formed by winding a suitable material such as stainless steel wire having a diameter of 0.007 inches on the portion 18a of the mandrel 18 having a diameter of 0.019 inches. The coil 26 is then coated with a suitable plastic material such as Teflon and is cut to a suitable length, as for example, 81.5 centimeters with one centimeter of the same near the distal extremity being uncoated and stretched for a screw together brazed joint as hereinafter described.

The guide wire 11 also includes a length of shrink tubing 31 having a suitable length as, for example, 45 centimeters as shown in FIG. 9 and having an outside diameter of approximately 0.41 inches and an inside diameter of approximately 0.026 inches.

With these fabricated components hereinbefore described, the guide wire may now be assembled. To start the assembly, the shrink tubing 31 is taken and is shrunk down onto the ground core element 12 approximately 100 centimeters from the distal tip of the core element 12. This can be accomplished in any suitable manner as, for example, by a batch process or by individual treatment of the shrink tubing with heat. The Teflon coated coil 26 is then placed on the core element 12 and bonded to the core element 12 at the point at which is juxtaposed to the distal extremity of the shrink tubing 31 by the use of a suitable material such as Cyanoacrylate. The coil or coil section 16 is then positioned on the core element 12 and its proximal extremity is threaded into the distal extremity of the Teflon coated coil 26 and thereafter a brazed joint 33 is formed to bond the juxtaposed ends of the coil 16 to the coil 26. The screw together joint 33 with the brazing is shown in FIG. 2. A gold alloy 33 can be utilized to form the joint 33. The use of gold which is radiopaque permits the doctor to see where the 0.035 portion of the guide wire 11 starts by the use of a fluoroscope. The coil 16 when so positioned on the core element 12 has its larger diameter wire beginning in a region closer to the proximal end and its smaller diameter wire ending in a region closer to the distal end.

The platinum coil 23 is then taken and its proximal extremity is positioned on the core element 12 and threaded into the distal extremity of the coil or coil section 16. After they have been screwed together, a suitable solder can be utilized for forming a joint 34 between the juxtaposed ends of the coils 23 and 16 and also to bond the same to the distal extremity of the core element 12. A tip 36 which has a rounded configuration is then provided on the distal extremity of the platinum coil 23.

After these assembly operations been completed, a torquer 38 of a conventional construction is mounted on the proximal extremity of the polyethylene shrink tubing 31. The torquer 38 firmly grasps the guide wire 11 and makes it possible for a physician by use of a hand to apply torque to the guide wire. The guide wire can have a suitable overall length as, for example, a length of 145 centimeters.

The operation and use of the guide wire 11 is very similar to that for other guide wires. It, however, has numerous characteristics which are particularly adapted to particular types of operations as, for example, where it is desired to make deeper penetration into the kidney of the human body. It also has a very small diameter tip while still having a relatively large diameter proximal to the tip to facilitate tracking of the catheter under the fluoroscope. The tapering of the coils or coil sections is particularly important and is made possible by the use of a tapered wire which is utilized for forming the tapered coil or coil sections. In addition, the screw together joints between the coil sections provides for transitions between the coil sections while still providing a smooth exterior circumferential surface.

It is apparent from the foregoing that there has been provided a new and improved guide wire which has a progressively attenuated diameter and which has good torsional capabilities. It also has a construction which can be economically manufactured in quantity with great precision. Even though a tapered tip sub assembly has been provided in connection with a Teflon coated coil and polyethylene shrink tubing, there is a very smooth transition provided between the different materials utilized in the guide wire facilitating its use in connection with small vessels in humans.

What is claimed is:

1. In a guide wire having a progressively attenuated diameter, an elongated core element having proximal and distal ends and having a decreasing cross sectional area in a direction towards the distal end, a coil carried by, surrounding and secured to said core element, said coil having proximal and distal ends, said coil having a diameter which decreases in a direction towards the distal end, said coil being formed of a wire which has a diameter which decreases from one end to the other end and which is wound in a helix so that the larger diameter wire begins in a region closer to the proximal end and the smaller diameter wire ends in a region closer to the distal end.

2. A guide wire as in claim 1 together with an additional coil formed of a radiopaque material having an end juxtaposed to the distal extremity of the first named coil.

3. A guide wire as in claim 2 wherein said additional coil has a substantially uniform diameter together with a rounded tip carried by the distal extremity of the additional coil.

4. A guide wire as in claim 3 wherein the juxtaposed ends of the first named and additional coils are screwed together and are bonded to the core element.

5. A guide wire as in claim 2, together with a second additional coil having proximal and distal ends carried by the core element and having its distal end juxtaposed to the proximal end of the first named coil and means forming a bond between the juxtaposed ends of the first named and second additional coil and the core element.

6. A guide wire as in claim 5 wherein said second additional coil is covered with a plastic coating.

7. A guide wire as in claim 5 together with polyethylene tubing carried by the proximal extremity of the core element and having its distal extremity juxtaposed to the proximal extremity of the second additional coil.

8. A guide wire as in claim 1 wherein said elongated core element has cylindrical portions of different diameters and tapered portions of different diameters adjoining said cylindrical portions.

9. A guide wire as in claim 8 wherein said coil is formed of a wire having cylindrical portions of different diameters with tapered portions of different diameters adjoining the same.

* * * * *